United States Patent [19]

Pawloski

[11] 4,196,293

[45] Apr. 1, 1980

[54] O,O-BIS(SUBSTITUTED PYRIDINYL)PHOSPHONATES AND PHOSPHONOTHIOATES

[75] Inventor: Chester E. Pawloski, Bay City, Mich.

[73] Assignee: The Dow Chemical Company, Midland, Mich.

[21] Appl. No.: 965,544

[22] Filed: Dec. 1, 1978

[51] Int. Cl.$^2$ .................... C07F 9/38; C07F 9/40

[52] U.S. Cl. .................... 546/25; 424/200

[58] Field of Search .................... 546/25

[56] References Cited

U.S. PATENT DOCUMENTS 4,115,557 9/1978 Pawloski .................... 424/200

FOREIGN PATENT DOCUMENTS 1165293 9/1969 United Kingdom .................... 546/25

*Primary Examiner*—Natalie Trousof

*Attorney, Agent, or Firm*—S. Preston Jones; Ronald G. Brookens

[57] ABSTRACT

O,O-bis-(pyridinyl)phosphonates and phosphonothioates corresponding to the formula:

$$\left[ X_n\text{-(pyridinyl)-O} \right]_2 \overset{\overset{\displaystyle Y}{\|}}{P}\text{—Z}$$

wherein X represents hydrogen, chloro, bromo, fluoro, trifluoromethyl or methyl; n represents an integer of from 1 to 3; Y represents oxygen or sulfur; and Z represents alkyl of 2 to 3 carbon atoms, haloalkyl of 1 to 2 carbon atoms with halo being chloro, fluoro or bromo, ethenyl, phenyl, phenylmethyl or cyclohexyl are prepared. These compounds have been found to have utility as insecticides.

8 Claims, No Drawings

O,O-BIS(SUBSTITUTED PYRIDINYL)PHOSPHONATES AND PHOSPHONOTHIOATES

FIELD OF THE INVENTION

This invention relates to insecticidal O,O-bis(-pyridinyl)phosphonates and phosphonothioates corresponding to the formula

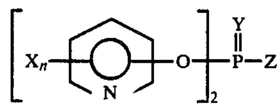

wherein X represents hydrogen, chloro, bromo, fluoro, trifluoromethyl or methyl; n represents an integer of from 1 to 3; Y represents oxygen or sulfur; and Z represents alkyl of 2 to 3 carbon atoms, haloalkyl of 1 to 2 carbon atoms with halo being chloro, fluoro or bromo, ethenyl, phenyl, phenylmethyl or cyclohexyl.

DESCRIPTION OF THE PRIOR ART

Various phosphorus-containing insecticides such as O-(6-chloro-2-pyridinyl)O-ethylphenylphosphonothioate taught in U.S. Pat. No. 4,115,557, patented Sept. 19, 1978, are known.

SUMMARY OF THE INVENTION

The present invention is directed to O,O-bis-(pyridinyl)phosphonates and phosphonothioates corresponding to the formula

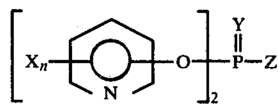

wherein X represents hydrogen, chloro, bromo, fluoro, trifluoromethyl or methyl; n represents an integer of from 1 to 3; Y represents oxygen or sulfur; and Z represents alkyl of 2 to 3 carbon atoms, haloalkyl of 1 to 2 carbon atoms with halo being chloro, fluoro or bromo, ethenyl, phenyl, phenylmethyl or cyclohexyl. These compounds have been found to be active insecticides.

The compounds of the present invention are oily liquids or solids at ambient temperatures and are soluble in many common organic carriers such as, for example, carbon tetrachloride, acetone, toluene, methylene chloride, dimethylformamide and the like.

Preferred compounds of the present invention include, for example, O,O-bis(6-fluoro-2-pyridinyl) ethylphosphonothioate, O,O-bis(6-trifluoromethyl)-2-pyridinyl ethylphosphonothioate, O,O-bis(6-fluoro-2-pyridinyl) chloromethylphosphonothioate, O,O-bis(6-fluoro-2-pyridinyl) propylphosphonothioate, O,O-bis(6-fluoro-2-pyridinyl) phenylphosphonothioate, O,O-bis(6-fluoro-2-pyridinyl) phenylmethylphosphonothioate, O,O-bis(6-fluoro-2-pyridinyl) bromoethylphosphonothioate, O,O-bis(6-fluoro-2-pyridinyl)cyclohexylphosphonothioate, O,O-bis(2-pyridinyl) ethylphosphonothioate, O,O-bis(6-bromo-2-pyridinyl) ethylphosphonothioate, O,O-bis(5-chloro-2-pyridinyl) ethylphosphonothioate, O,O-bis(6-chloro-2-pyridinyl) ethylphosphonothioate, O,O-bis(5,6-dichloro-2-pyridinyl) ethylphosphonothioate, O,O-bis(3,5-dichloro-2-pyridinyl) ethylphosphonothioate, O,O-bis(6-ethylthio-2-pyridinyl) ethylphosphonothioate, O,O-di(3-pyridinyl) ethylphosphonothioate, O,O-bis(6-chloro-2-pyridinyl) phenylphosphonothioate, O,O-bis(5 -chloro-2-pyridinyl) phenylphosphonothioate, O,O-bis(3,5,6-trichloro-2-pyridyl) ethylphosphonothioate, O,O-bis(6-methyl-3-pyridinyl) ethylphosphonothioate, O,O-bis(5-bromo-2-pyridyl) ethylphosphonothioate.

The compounds of the present invention can be prepared by the reaction of an appropriate substituted pyridinol with either a phosphonic dichloride or with a phosphonothioic dichloride in the presence of an inert organic carrier (solvent).

The reaction can be characterized as follows:

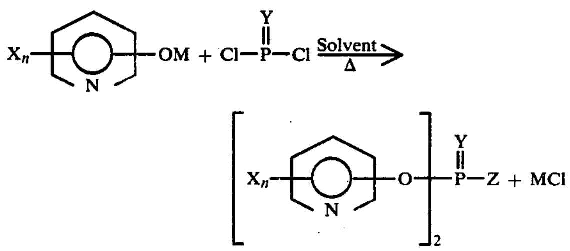

wherein X, n, Y and Z are as hereinbefore set forth and M is sodium, calcium, cesium, lithium or potassium. It should be noted that no attempt has been made to present a balanced equation.

The reaction is preferably carried out in the presence of an inert carrier medium such as, for example, benzene, toluene, xylene, acetone, methylisopropyl ketone, methylisobutyl ketone, acetonitrile, dimethylformamide, methylene chloride and the like. The reaction is further preferably carried out in the presence of an acid acceptor. For this purpose, the customary acid-binding agents can be employed. Those that are particularly suitable include, for example, alkali metal alcoholates and carbonates, such as potassium and sodium methylate or ethylate, sodium and potassium carbonate and tertiary amines such as, for example, triethylamine, trimethylamine, pyridine and the like. A small amount of a catalyst, such as mercurous chloride, preferably trimethylbenzylammonium chloride, and the like is also preferably employed.

Ordinarily, a solution or suspension of an alkaline salt of the substituted pyridinol reactant is first prepared and subsequently reacted with an appropriate substituted phosphonic or phosphonothioic dichloride. The reactants, and acid-acceptor are, in general, employed in stoichiometric amounts of two molar proportions of the pyridinol reactant and acceptor to one molar proportion of the dichloride reactant. The reaction temperature can be varied over a fairly wide range and, in general, the reaction is carried out at temperatures of from about 0° to about 100° C. (or the boiling point of the reaction mixture). Generally, the reaction is carried out, with agitation, for a period of from about one to about eight hours. The crude product is usually obtained in the form of a viscous oil or solid which can be freed from volatile impurities by heating at moderately elevated temperatures under reduced pressure and recrystallized from an appropriate solvent.

The following non-limitative examples further illustrate the invention.

EXAMPLE 1

O,O-bis(6-fluoro-2-pyridinyl) ethylphosphonothioate

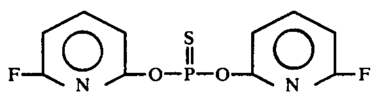

Into a 500 milliliter (ml) flask were placed 22 grams (g) (0.15 mole (m)) of the sodium salt of 6-fluoro-2-pyridinol, 1 gram $HgCl_2$ and 200 milliliters of acetonitrile. The mixture was stirred while 9.5 grams (0.075 mole) of ethylphosphonothioic dichloride was added. An exotherm from 24° C. to 38° C. was obtained. The mixture was stirred at 40°–45° C. for five hours and allowed to cool. The insolubles were filtered off and the liquid phase distilled under reduced pressure until all the solvent was removed. The resulting oil was taken up in 300 milliliters of methylene chloride and washed once with 200 milliliters of water, once with 200 milliliters of aqueous 2% NaOH and twice with 200 milliliters portions of water. The product layer was dried over sodium sulfate, filtered and distilled under reduced pressure at 45° C. until the solvent was removed. The resulting oil was mixed in 150 mls of n-hexane and cooled to dry ice/acetone bath temperatures. The resulting solids were filtered off and dried to give a 60% yield of O,O-bis(6-fluoro-2-pyridinyl) ethylphosphonothioate, a solid, m.p. 47°–49° C. Product was confirmed by N.M.R. and I.R. spectra (compound No. 1).

Employing an alternative procedure, the same compound was prepared as follows:

Into a three liter flask were placed 523 grams (4.6 moles) of 6-fluoro-2-pyridinol, 638 grams (4.6 moles) potassium carbonate, 1.0 grams $HgCl_2$ and two liters of acetonitrile. The mixture was stirred at 50°–55° C. for two hours and allowed to cooled. The mixture was stirred while 269 grams (2.1 moles) of ethylphosphonothioic dichloride was added dropwise. An exotherm from 25° C. to 55° C. was obtained. The mixture was stirred at 50° C. for five hours and allowed to cool. The insolubles were filtered off and the solvent removed under reduced pressure at 45° C. The resulting oil was taken up in 1.5 liters of methylene chloride and washed once with one liter of water, once with one liter of aqueous 2% NaOH and again with one liter of water. The product layer was dried over sodium sulfate, filtered and the solvent removed under reduced pressure at 45° C. The resulting oil was poured into 250 milliliters of cold n-hexane and stirred. The solid product was filtered off and dried to give a 52% yield of the desired O,O-bis(6-fluoro-2-pyridinyl) ethylphosphonothioate, m.p. 46°–48° C. (compound No. 1).

Additional compounds of the present invention are similarly prepared according to the procedures of Example 1 above by employing the appropriate substituted 2- or 3-pyridinol and the appropriate substituted phosphonic or phosphonothioic dichloride reactants. Such other compounds include the following compounds:

O,O-bis(6-trifluoromethyl)-2-pyridinyl ethylphosphonothioate, melting at 64°–66° C. (compound No. 2);

O,O-bis(6-fluoro-2-pyridinyl) chloromethylphosphonothioate, melting at 103°–106° C. (compound No. 3);

O,O-bis(6-fluoro-2-pyridinyl) ethylphosphonate, having a refractive index n/D of 1.5290 at 25° C. (compound No. 4);

O,O-bis(6-fluoro-2-pyridinyl) propylphosphonate, having a refractive index n/D of 1.5137 at 25° C. (compound No. 5);

O,O-bis(6-fluoro-2-pyridinyl) propylphosphonothioate, melting at 82°–85° C. (compound No. 6);

O,O-bis(6-fluoro-2-pyridinyl) phenylphosphonothioate, melting at 58°–60° C. (compound No. 7);

O,O-bis(6-fluoro-2-pyridinyl) phenylmethylphosphonothioate, melting at 38°–41° C. (compound No. 8);

O,O-bis(6-fluoro-2-pyridinyl) chloromethylphosphonate, melting at 45°–54° C. (compound No. 9);

O,O-bis(6-fluoro-2-pyridinyl) bromoethylphosphonothioate, melting at 64°–71° C. (compound No. 10);

O,O-bis(6-fluoro-2-pyridinyl) cyclohexylphosphonothioate melting at 75°–78° C. (compound No. 11);

O,O-bis(5-bromo-2-pyridinyl) ethylphosphonothioate, melting at 115°–118° C. (compound No. 12);

O,O-bis(2-pyridinyl) ethylphosphonothioate, melting at 70°–72° C. (compound No. 13);

O,O-bis(6-bromo-2-pyridinyl) ethylphosphonothioate, melting at 69°–71° C. (compound No. 14);

O,O-bis(5-chloro-2-pyridinyl) ethylphosphonothioate, melting at 84°–87° C. (compound No. 15);

O,O-bis(6-chloro-2-pyridinyl) ethylphosphonothioate, melting at 75°–76° C. (compound No. 16);

O,O-bis(5,6-dichloro-2-pyridinyl) ethylphosphonothioate, melting at 106°–109° C. (compound No. 17);

O,O-bis(3,5-dichloro-6-fluoro-2-pyridinyl) ethylphosphonothioate, melting at 66°–70° C. (compound No. 18);

O,O-bis(6-ethylthio-2-pyridinyl) ethylphosphonothioate, melting at 69°–71° C. (compound No. 19);

O,O-di(3-pyridinyl) ethylphosphonothioate, having a refractive index, n/D 1.5803 at 25° C. (compound No. 20);

O,O-bis(6-chloro-2-pyridinyl) phenylphosphonothioate, melting at 63°–66° C. (compound No. 21);

O,O-bis(5-chloro-2-pyridinyl) phenylphosphonothioate, melting at 117°–120° C. (compound No. 22);

O,O-bis(3,5,6-trichloro-2-pyridyl) ethylphosphonothioate, melting at 88°–90° C. (compound No. 23);

O,O-bis(6-methyl-3-pyridinyl) ethylphosphonothioate, having a refractive index n/D of 1.5672 (compound No. 24);

O,O-bis(6-fluoro-2-pyridinyl) cyclohexylphosphonate, melting at 69°–72° C. (compound No. 25);

O,O-bis(6-fluoro-2-pyridyl) ethenylphosphonate, melting at 37°–47° C. (compound No. 26);

The active ingredients of this invention have been found to be active against insect pests including beet army worms, German roach, western spotted cucumber beetle, lone star tick, brown dog tick, cayenne tick, American dog tick, flies, including blow fly and horn fly, tobacco budworm and two-spotted spider mite. For such uses, unmodified actived ingredients of the present invention can b. employed. However, the present invention embraces the use of a pesticidally-effective amount of the active ingredients in composition form with an inert material known in the art as an adjuvant or carrier in solid or liquid form. Such compositions are employed to contact the insect organism and/or its habitat. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersion, with or without the addition of wetting, dispersing, or emulsifying agents.

Suitable adjuvants of the foregoing type are well known to those skilled in the art. The methods of applying the solid or liquid pesticidal formulations similarly are well known to the skilled artisan.

As organic solvents used as extending agents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl and ethyl ether and diethylene glycol monomethyl ether, alcohols, e.g., methanol, ethanol, isopropanol, amyl alcohol, ethylene glycol, propylene glycol, butyl carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freon® and Genetron® dispersants, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions utilizing the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and resin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 surfactant (molecular weight 1000), polyethylene glycol ester of tall oil acids, sodium octyl phenoxyethoxy ethyl sulfate, Tween 60, tris (polyoxyethylene)sorbitan monostearate, and sodium dihexyl sulfosuccinate.

The active ingredients of the invention may be present in the formulations in admixture with other active compounds.

The formulations contain, in general, from about 0.0001 to about 95; preferably from about 0.01 to about 90, percent by weight of active compounds, The concentration of active ingredient varies depending upon the intended use. In general, concentrations of at least about 0.0002 percent are employed for control of southerm house mosquito larvae while concentrations of at least about 0.01 percent are employed for control of the above listed ticks. Concentrations of at least about 0.001 percent and 0.04 are employed for control of copper bottle flies and beet armyworm larvae, respectively. Such formulations can be applied by spraying, dusting, etc.

In practice, the active compound is distributed so as to provide contact of the target insect with toxic amounts of the active compound. Such contact can be achieved through direct contact of the active compound with the target insect of by more indirect means such as by application to its food and/or habitat. Thus, for example, an active compound hereof or a composition thereof can be spread throughout the environs of the target host so as to provide both direct and indirect contact thereof or bait compositions incorporating a toxic amount of an active compound or composition thereof can be readily prepared and strategically located so as to provide ultimate contact of the host species therewith.

The following additional examples serve to typify further the nature of the present invention and are given solely for the purpose of illustration.

EXAMPLE 2

Twenty-five parts by weight of one of the compounds numbered 9, 12, 16, 17, 18, 19, 20, 23, 24 and 25, 60 parts of fuller's earth, 10 parts of diatomaceous earth, 3 parts of an alkyl aryl sulfonate (Naccanol NR) and 2 parts of a polymerized sodium salt of a substituted benzoid alkyl sulfonic acid (Daxad No. 27) are mechanically mixed and groundtogether to prepare a concentrate composition in the form of a wettable powder.

Similarly, 25 parts by weight of one of the compounds numbered 1, 3, 5, 7, 8 and 26, 65 parts xylene and 10 parts of a dimeric alkylated aryl polyether alcohol (Triton X-155), are mechanically mixed together to prepare a liquid emulsifiable concentrate composition.

In a like manner, 6 parts by weight of one of the compounds numbered 2, 4, 6, 10, 11, 12, 13, 14, 15 and 21, 2 parts of Naccanol NR, 2 parts of Daxad No. 27, and 200 parts of water are ballmilled together to prepare a concentrate composition in the form of a water-dispersible liquid.

EXAMPLE 3

One part of one of the compounds numbered 2, 4, 6, 8, 11, 14, 16, 19, 20 and 25 is mixed with 99 parts of purified kerosene to obtain an oil preparation having an active ingredient concentration of 1 percent. In application, the composition can be atomized or sprayed as is.

These concentrate compositions may be further diluted in their concentrate state and/or dispersed in water to prepare aqueous compositions which have desirable wetting and penetrating properties. These compositions are adapted to be employed to treat target insect life and thus distribute active compound to provide contact of such insect life in insecticidal concentrations.

In view of the foregoing and the following additional disclosures, one skilled in the art can readily determine the optimum rate to be applied in any particular case. So as to illustrate the properties of the active ingredients, a group of controlled experiments was carried out using the following test methods:

EXAMPLE 4

Copper Bottle Fly (Blowfly)

One and one-half milliliters of an acetone solution containing 10 ppm of active compound was innoculated and absorbed onto cotton plugs and placed into vials. The treated plugs were allowed to stand for 24 hours to allow the acetone to evaporate, thereby leaving the active ingredient on the cotton plug. One milliliter of bovine serum was innoculated into the cotton plugs as a feeding medium and 50–100 first stage copper bottle fly or blowfly maggots at 1–6 hours of age were placed on the treated plug. The vials were then capped with cotton and maintained at a temperature of 82°–84° F. and 80 percent relative humidity for a period of 24 hours. The vials were then examined. Mortality of larvae when compound Nos. 2 and 6 were so tested was 100%.

EXAMPLE 5

German Cockroach

Cylindrical cartons about 3⅝ inches in diameter by 3¼ inches high were fitted with wire screen on the top and bottom. Into each cage was placed a predetermined number of German cockroaches. An aqueous dispersion prepared by admixing one of the active ingredients with a predetermined amount of water and a surfactant, was sprayed on the cockroaches through the screen from a distance of about 15 inches using a fine spray nozzle. At the same time, additional cockroaches were sprayed with a water-surfactant mixture containing no active toxicant to serve as controls. After spraying, the cockroaches were fed a sugar-water diet for 2 days. At the end of this period, the cages were examined to determine the minimum concentration in parts of active compound per million parts of the ultimate compostion (ppm) necessary to give at least a 100 percent ($LD_{100}$) kill and control of the cockroaches. Compound Nos. 2 and 4 at 400 ppm and Compound No. 3 at 100 ppm gave a 100% kill when so tested.

EXAMPLE 6

Western Spotted Cucumber Bettle

Seventy-five grams of air-dried soil was placed in an 8-ounce container. To the soil was added sufficient volume of a 400 ppm aqueous dispersion, prepared by admixing a predetermined amount of one of the active ingredients dissolved in a suitable solvent with a predetermined amount of water and a predetermined amount of a surfactant, to give various predetermined concentrations of the active ingredient in the soil on a soil-chemical basis. The treated soil was air-dried and thoroughly mixed with a spatula. To each treated container, and control containers treated with water and surfactant alone, was added 0.5 milliliter of an aqueous suspension of the eggs of the Western spotted cucumber beetle (WSCB) (70–80 eggs, 3–4 days old). Additional treated soil was used to cover the eggs and a sprouted corn seed was placed on the soil and covered with additional treated soil. The containers were thereafter maintained under conditions conducive to the growth of the seeds and the hatching of the eggs (75°–80° F.). Ten to twelve days after treatment, the containers and the plants therein were examined to determine the minimum concentration in parts of active ingredient per million parts of the ultimate dispersion necessary to give at least a 100 percent kill and control of the larvae from the hatched eggs. Compound Nos. 2, 3, 6, 13, 14 and 21 gave a 100% kill at 25 ppm when so tested.

EXAMPLE 7

Beet Armyworm

In this operation, aqueous dispersions were prepared by admixing one of the active ingredients dissolved in a suitable solvent with a predetermined quantity of water and a predetermined amount of a surfactant to give aqueous dispersions containing varying predetermined amounts of one of the compounds as the sole active toxicant. Separate cotton plant leaves were thoroughly wetted briefly by dipping into one of the dispersions and the wetted leaves placed in an open Petri dish and permitted to dry. After the leaves were dry, 5 live armyworm larvae, approximately late second instar were placed in each Petri dish. In identical operations, 5 live and late second instar beet armyworm larvae were placed in conrol Petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the minimum concentration in parts of the active ingredient per million parts of the ultimate dispersion necessary to five at least a 60 percent kill and control of the beet armyworm larvae. When so tested, compound Nos. 1, 2, 3, 11, 14 and 19 at 400 ppm gave 100% kills, compound Nos. 6 and 15 at 100 ppm gave 100% kills and compounds 8, 25 and 26 at 400 ppm gave at least a 60% kill.

EXAMPLE 8

Tobacco Budworm

In this operation, aqueous dispersions were prepared by admixing one of the hereinabove set forth compounds dissolved in a suitable solvent with a predetermined quantity of water and a predetermined amount of a surfactant to give aqueous dispersions of varying predetermined amounts of one of the compounds as the sole active toxicant. Separate 3-inch disc cut from tobacco plant leaves were thoroughly wetted briefly by dipping into one of the dispersions and the wetted leaves placed in an open Petri dish and permitted to dry. After the leaves were dry, 5 live tobacco budworm larvae approximately late second instar were placed in each Petri dish. In identical operations, 5 live tobacco budworm larvae were placed in control Petri dishes, the leaf therein having been wetted with a solution containing only water and surfactant. The dishes were maintained under moist conditions and at 80° F. conducive for the growth of the tobacco budworm larvae for a period of about 2 days. At the end of the 2-day period, the dishes were examined to determine the minimum concentration in parts of the active ingredient per million parts of the ultimate dispersion necessary to give at least a 67 percent kill and control of the tobacco budworm larvae. When so tested, compound Nos. 2 and 14 at 400 ppm and compound No. 5 at 100 ppm gave 100% kills.

EXAMPLE 9

Two-Spotted Spider Mites

Aqueous dispersions were prepared by admixing one of the active ingredients with a predetermined quantity of water and a predetermined amount of a surfactant to give aqueous dispersions containing varying predetermined amounts of one of the active ingredients as the sole toxicant. Separate wild mustard plants were infested with 20 two-spotted spider mites and the plates sprayed with one of the dispersions to run off. In a like manner, 20 two-spotted spider mites were placed on control plants and the plants sprayed to run off with a solution containing only water and surfactant. The plants were maintained under conditions conducive to the growth of the plants and mites. After a period of two days, the plants were examined to determine the minimum concentration in parts of the active compound per million parts of the ultimate dispersion necessary to give at least 83 percent kill and control of the mites. Compound Nos. 1, 5, 12, 22 and 23 at 400 ppm equalled or exceeded such control.

EXAMPLE 10

Ticks

Predetermined amounts of an active ingredient are made into acetone solutions from a 20 percent silica gel formulation. Ticks are dipped into the solution for approximately 3 seconds, dried, and placed in vials. Mortality readings for lone star tick, cayenne tick, American dog tick, and brown dog tick are made on the fourth day after treatment. Results are recorded as 0 to 100 percent. When so tested, compound Nos. 1 and 16 gave 100% kills of lone star tick, cayenne tick and American dog tick at (1) 10, 10 and 100 ppm and (16) 30, 30 and 100 ppm, respectively.

EXAMPLE 11

Hornfly

Manure samples from cattle were collected and frozen to kill any wild insect larvae that may have been present. The samples were thawed and mixed with an aqueous dispersion of compound Nos. 3, 8, 10 or 19 to provide a sample of each containing 10 parts of one of the compounds per million parts of the ultimate mixture. The treated samples and a sample containing no toxicant, to serve as control, were each seeded with ~500 hornfly eggs. The samples were incubated at 80° F. for 15 days to provide sufficient time for the eggs to hatch. The percent control was determined by counting the number of normal adult flies that hatched from the treated samples and comparing this figure with the number of flies that hatched from the untreated (control) sample. It was determined that there was, in each of the treated samples, a 100% control of hornflies.

I claim:

1. A compound having the formula:

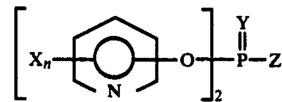

wherein X represents hydrogen, fluoro, chloro, bromo, trifluoromethyl or methyl; n represents an integer from 1 to 3; Y represents oxygen or sulfur; and Z represents $C_{2-3}$ alkyl, haloalkyl of 1 to 2 carbon atoms with halo being fluoro, chloro or bromo, ethenyl, phenyl, phenylmethyl or cyclohexyl.

2. A compound as claimed in claim 1 wherein Y represents S.

3. A compound as claimed in claim 2 wherein $X_n$ represents 6-fluoro.

4. The compound of claim 2 which is O,O-bis(6-fluoro-2-pyridinyl) ethylphosphonothioate.

5. The compound of claim 2 which is O,O-bis(6-fluoro-2-pyridinyl) propylphosphonothioate.

6. The compound of claim 2 which is O,O-bis(6-trifluoromethyl-2-pyridinyl) ethylphosphonothioate.

7. The compound of claim 2 which is O,O-bis(6-fluoro-2-pyridinyl) chloromethylphosphonothioate.

8. The compound of claim 2 which is O,O-bis(6-bromo-2-pyridinyl) ethylphosphonothioate.

* * * * *